United States Patent [19]

Samuels et al.

[11] Patent Number: 5,977,405
[45] Date of Patent: Nov. 2, 1999

[54] PREPARATION OF AROMATIC HYDROXYCARBOXYLIC ACIDS AND DIALKALI METAL SALTS THEREOF

[75] Inventors: Michael Robert Samuels; Ronald M. Yabroff, both of Wilmington, Del.

[73] Assignee: E. I. du Pont de Nemours and Company, Wilmington, Del.

[21] Appl. No.: 09/189,599

[22] Filed: Nov. 10, 1998

Related U.S. Application Data

[62] Division of application No. 08/832,738, Apr. 4, 1997.

[51] Int. Cl.$^6$ ............................. C07C 51/15; C07C 37/68
[52] U.S. Cl. ............................................. 562/424; 568/749
[58] Field of Search .............................. 562/424; 568/749

[56] References Cited

U.S. PATENT DOCUMENTS

| | | | |
|---|---|---|---|
| 3,435,068 | 3/1969 | Gehring et al. | 260/521 |
| 4,272,635 | 6/1981 | Siegel et al. | 568/776 |
| 4,451,330 | 5/1984 | Vitner | 159/48.2 |
| 4,966,992 | 10/1990 | Ueno et al. | 562/424 |

FOREIGN PATENT DOCUMENTS

| | | | |
|---|---|---|---|
| 0 436 379 A2 | 10/1991 | European Pat. Off. | C07C 51/15 |
| 0 625 500 A1 | 5/1993 | European Pat. Off. | C07C 51/15 |
| 47-34693 | 9/1972 | Japan . | |
| 169948 | 1/1989 | Taiwan . | |

*Primary Examiner*—Paul J. Killos

[57] ABSTRACT

Alkali metal aryloxides may be speedily dried by removing water while the aryloxide is molten. Such dried alkoxides are useful as chemical intermediates. Molten alkali metal aryloxides may be contacted with carbon dioxide to quickly produce the dialkali metal salts of aromatic hydroxycarboxylic acids, which upon acidification yield the corresponding aromatic hydroxycarboxylic acids. Aromatic hydroxycarboxylic acids are useful as chemical intermediates and as monomers for polymers. Solid metal aryloxides may be reacted with carbon dioxide in a reactor in which the contents, even when pasty, may be agitated so that the reaction is more rapid than in prior methods.

23 Claims, 2 Drawing Sheets

PREPARATION OF AROMATIC HYDROXYCARBOXYLIC ACIDS AND DIALKALI METAL SALTS THEREOF

This is a division of application Ser. No. 08/832,738 filed Apr. 4, 1997.

FIELD OF THE INVENTION

This invention concerns processes for drying alkali metal aryloxides and/or reacting alkali metal aryloxides with carbon dioxide. These processes are useful for the preparation of aromatic hydroxycarboxylic acids.

BACKGROUND OF THE INVENTION

Aromatic hydroxycarboxylic acids are used as chemical intermediates for the synthesis of drugs and antimicrobials, as well as monomers for preparing polyesters. For instance o-hydroxybenzoic acid (OHBA, salicylic acid) is used as a chemical intermediate, for instance to make aspirin, while p-hydroxybenzoic acid (PHBA) is used to make parabens and is also used as a monomer in making polyesters. They can be prepared using alkali metal aryloxides.

Alkali metal aryloxides are usually prepared by the reaction of an aryl hydroxy compound such as phenol with an alkali metal containing base, such as sodium or potassium hydroxide. This may be done in the presence of water, and in addition water is produced in the reaction.

These aryloxides are useful as chemical intermediates for a variety of chemical processes such as the Kolbe-Schmitt process to make hydroxycarboxylic acids, see for instance, A. S. Lindsey, et al., Chem. Rev., vol. 57, p. 583–620 (1957). For some of these processes it is desirable to remove essentially all of the water from the aryloxide. This is typically done by heating the solid aryloxide (or initially an aqueous solution of the aryloxide which eventually becomes solid) while applying a vacuum and/or passing an inert dry gas over the aryloxide. However, this is quite time-consuming, and therefore expensive, and thus improved drying methods would be advantageous.

After the alkali metal aryloxide is dried it may be reacted with carbon dioxide to (usually) form a dialkali metal salt of aromatic hydroxycarboxylic acid which may be converted to the free hydroxyacid by reaction with a strong acid, such as sulfuric acid. This is usually done by exposing powdered alkali metal aryloxide to carbon dioxide for long periods of time, often in an apparatus in which the solid (or the resulting paste which is formed during the reaction) may be ground in order to expose new solid surface for reaction with the $CO_2$. Thus, improved carboxylation procedures for the Kolbe-Schmitt reaction are of commercial interest.

Canadian Patent 881,906 and U.S. Pat. No. 3,554,264 describe a process for drying alkali metal phenates in a spray drying column in which the drying gas enters the column at 250 to 500° C. No mention is made that the temperature of the alkali metal phenoxide reaches above the melting point of the phenoxide, nor that the dry phenoxide is ever a liquid.

SUMMARY OF THE INVENTION

A process of this invention for drying an alkali metal aryloxide, comprises finally removing water from said alkali metal aryloxide while said alkali metal aryloxide is molten.

Further, a process of this invention for producing a dialkali metal salt of an aromatic hydroxycarboxylic acid, comprises, contacting, at a temperature about or above the melting point of an alkali metal aryloxide, said alkali metal aryloxide with carbon dioxide.

Another process of this invention for producing a dialkali metal salt of an aromatic hydroxycarboxylic acid, comprises:

(a) finally removing water from an alkali metal aryloxide while said alkali metal aryloxide is molten; and (b) contacting, with agitation and at a temperature about or above the melting point of said alkali metal aryloxide, said alkali metal aryloxide with carbon dioxide.

The present invention also discloses and claims an improved process for the production of an aromatic hydroxycarboxylic acid using a Kolbe-Schmitt reaction of a metal salt of an aromatic hydroxy compound with carbon dioxide wherein a paste is produced during the reaction, wherein the improvement comprises, carrying out the reaction with carbon dioxide at a pressure of about 0.8 to 2 atmospheres, absolute, in a reactor whose contents are agitated and wherein there is sufficient free volume that a gas may pass relatively freely through the reactor and be contacted with solid and/or liquid ingredients present provided that:

the agitation is sufficient that the average residence time of a nongaseous reactant in said reactor is less than about 2 hours;

at least 80 mole percent of said metal salt of an aromatic hydroxy compound is reacted with said carbon dioxide in said reactor; and the gas which is unreacted exits the reactor.

DETAILED DESCRIPTION OF THE INVENTION

Figure 1:
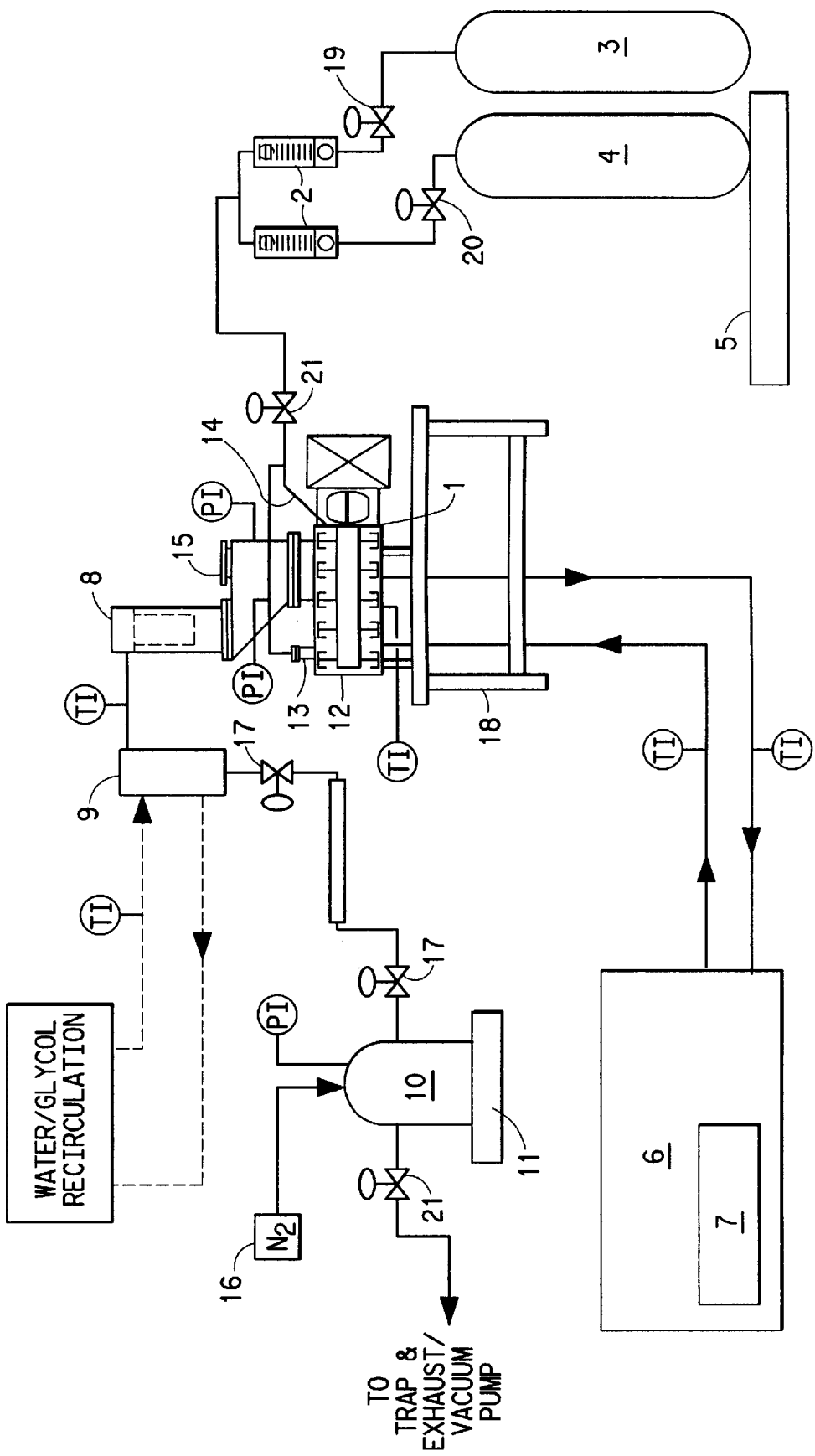
FIG. 1 is a schematic diagram of the apparatus used in Examples 1 and 5–7.

The compounds being dried herein are alkali metal aryloxides. By an alkali metal is meant any one of lithium, sodium, potassium, cesium or rubidium. Potassium and sodium are preferred alkali metals, and potassium is especially preferred. By an aryloxide is meant a monovalent anion of the structure Ar—O$^-$, wherein Ar is an aryl group or substituted aryl group wherein the oxygen is bound to a carbon atom of an aromatic ring. Without intending to limit the generality of the foregoing, useful aryl groups include phenyl, 1-naphthyl, 2-naphthyl, 2-phenylphenyl, and 3-methylphenyl. Preferred aryl groups are phenyl, 2-phenylphenyl, and 2-naphthyl and phenyl are more preferred, and phenyl is especially preferred.

Alkali metal aryloxides may be prepared by the reaction of a strong base (stronger than aryloxide anion) with a corresponding aromatic hydroxy compound, Ar—OH. A suitable base is an alkali metal hydroxide, which is often also relatively inexpensive. This reaction may be carried out in water or by reacting solid alkali metal hydroxide (which usually contains some water) with a molten aromatic hydroxy compound, typically by using approximately equivalent amounts of aromatic hydroxy compound and alkali metal hydroxide. For instance, 45% aqueous KOH may be reacted with phenol.

By drying herein is meant the removal of water from an alkali metal aryloxide. It is preferred that the final "dry" aryloxide have a water content of less than 2000 ppm water, preferably less than 500 ppm water, and more preferably less than 100 ppm water. In a typical drying process currently practiced in the art, an aqueous solution of an alkali metal aryloxide is heated to distill or vaporize off the water. Eventually the concentration of the alkali metal aryloxide becomes so high that it precipitates from the solution, and the final stages of drying are performed on the solid aryloxide. While water is being removed, a preferably dry, inert gas may be passed over the aryloxide, or the aryloxide may be subjected to a vacuum, or both, to help remove water vapor.

In the drying process disclosed herein, the last stages of drying are conducted at a high enough temperature so that the alkali metal aryloxide is molten. This means this final drying (i.e., the "last" water removed) is conducted at about or above the melting point of the dry alkali metal aryloxide. In one method of drying, the temperature of the aryloxide (and the accompanying water) are continuously raised until at or above the melting point of the aryloxide. During this time, what may have started as a one phase liquid containing water and aryloxide may be converted to a solid aryloxide or a solid and liquid, and then, if a solid had formed that solid will change back to a single phase liquid as the melting point of the aryloxide is approached and/or exceeded. During this time an inert gas may be passed over the aryloxide and/or a vacuum applied. Agitation of the aryloxide, whether solid or liquid, will usually help speed drying. The final removal of water takes place when the aryloxide is molten.

Another way of carrying out the drying is to heat the mixture of water and alkali metal aryloxide above the melting point of the aryloxide under atmospheric or elevated pressure, so sufficient water is present so that a single liquid phase is maintained. As the temperature approaches the melting point of the aryloxide the pressure may be lowered to allow the water to vaporize, and the drying is finished as described above. Care should be taken that the vaporization of water does not cool the liquid sufficiently so that a solid forms during the final drying stage.

Figure 2:
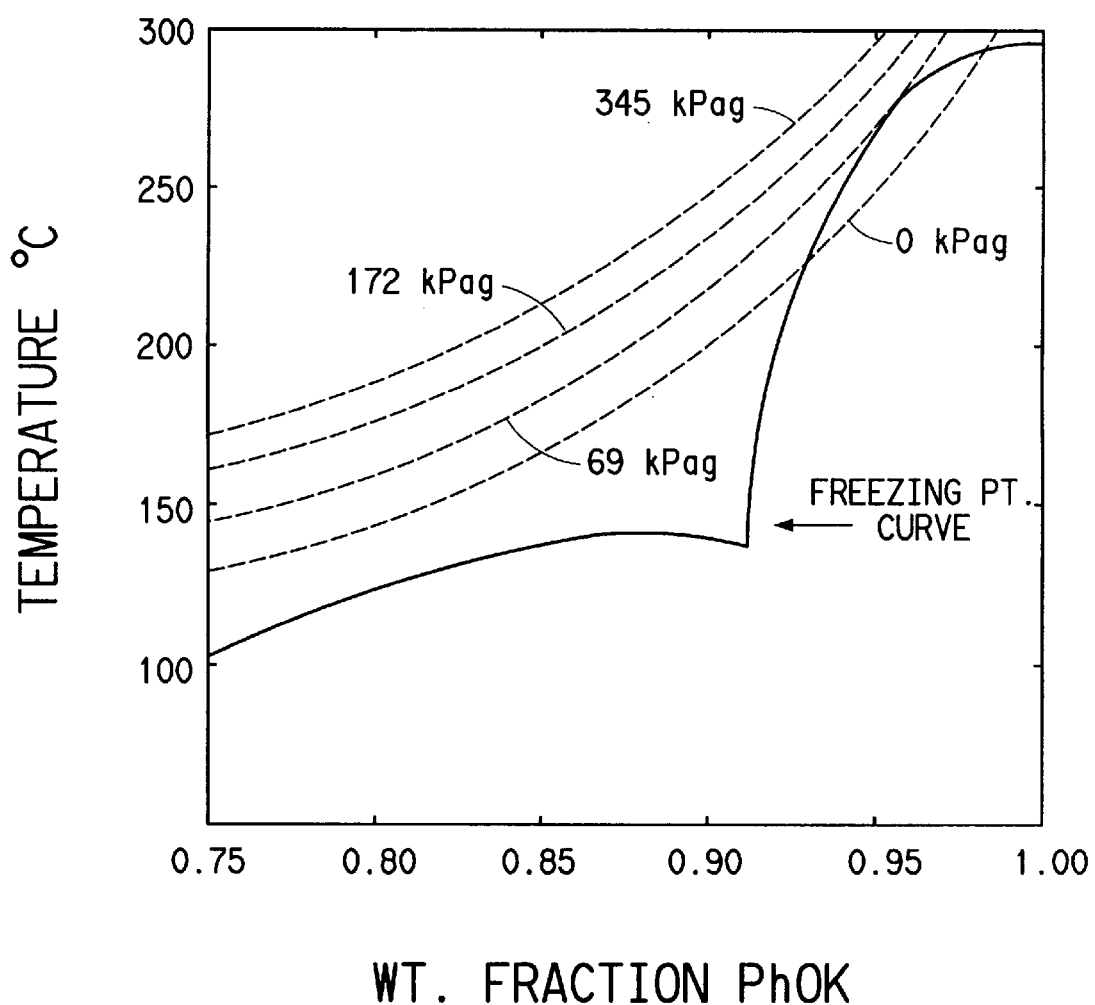
FIG. 2 is a freezing point diagram of the potassium phenoxide-water system which also shows the boiling point of the solutions at various pressures of water over the system.

The above discussion on dehydration of aryloxides is illustrated by the dehydration of potassium phenoxide, and the phase diagram associated with that dehydration which is shown in FIG. 2. This Figure was generated by appropriate measurements in the laboratory, but the data was smoothed and the curves at various pressures made parallel with the assumption that Henry's Law is followed at low partial pressures of water in the vapor phase. Therefore all data on this Figure should be considered approximate. The solid line shows the freezing point of the potassium phenoxide/water system. The abscissa is the weight fraction of potassium phenoxide present (water is the other part of the weight fraction), while the ordinate is temperature in degrees Centigrade. The dashed lines show the boiling points of the water in the system at the indicated pressures (0 psig or 0 kPag is atmospheric pressure). Where the freezing point curve is above the boiling point of the water in the system, as it is at 0 kPag (0 psig) and approximately 0.93 to 0.98 mass (weight) fraction of potassium phenoxide, the system will be partially a solid as the water is vaporized from the system. Above a mass (weight) fraction of about 0.98 potassium phenoxide the system will be a liquid as the water is removed at 0 kPag (0 psig). However, if the system pressure is held at about 68.9 kPag (10 psig) or higher, it will remain a liquid throughout the removal of the water.

Removal of the final amounts of water from molten alkali metal aryloxide usually proceeds rapidly, thereby making the drying process more economical.

It is of course preferred that the alkali metal aryloxide not decompose appreciably during the drying, i.e., be reasonably stable at or above its melting point. Therefore it is preferred that the alkali metal aryloxide have a melting point of less than 400° C., more preferably less than about 350° C., and especially preferably less than about 320° C. A preferred minimum drying temperature is either the melting point of the alkali metal aryloxide or 275° C., whichever is higher. The temperature referred to during the (last part of the) drying is the actual temperature of the alkali metal aryloxide itself. Melting points are determined by Differential Scanning Calorimetry at a rate of 25° C./min, and the melting point is taken as the extrapolated initial temperature of the melting endotherm.

Preferred alkali metal aryloxides are potassium phenoxide, sodium phenoxide, and potassium 2-naphthoxide, and potassium phenoxide is especially preferred.

The drying process may be carried out in any vessel suitable for use with the materials and temperatures involved. Stainless steel is particularly suitable. If part of the drying process is to be done under pressure and/or vacuum, the vessel should be so rated. It may be desirable to be able to stir the liquid and/or solid which may be present in the vessel, to improve heat transfer and promote vaporization of the water from the aryloxide. The vessel and its contents may be heated by the usual methods, such as a condensing vapor such as Dowtherm® heat transfer fluid (available from Dow Chemical Co., Midland, Mich.), electrically, or by hot oil.

The dry aryloxide which is produced may be cooled and solidified, and used in a traditional Kolbe-Schmitt-type process, or may remain molten and undergo reaction with $CO_2$ to form a dialkali metal salt of an aromatic hydroxycarboxylic acid.

The chemical reaction involved in the Kolbe-Schmitt synthesis may be represented as:

$$ArOH + MOH \rightarrow ArOM + H_2O \quad (1)$$

$$2ArOM + CO_2 \rightarrow M_2(OArCO_2) + ArOH \quad (2)$$

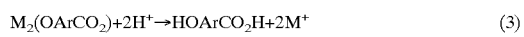

$$M_2(OArCO_2) + 2H^+ \rightarrow HOArCO_2H + 2M^+ \quad (3)$$

M in the above equations in an alkali metal, and Ar is an aryl, substituted aryl, substituted arylene, or arylene group, as appropriate. Equation (1) is simply the formation of an alkali metal aryloxide whose drying is described above. The "dry" aryloxide is reacted with $CO_2$ to usually form a dialkali metal salt of an aromatic hydroxycarboxylic acid. This salt may then be acidified to form an aromatic hydroxycarboxylic acid (sometimes referred to herein as the "free" aromatic hydroxycarboxylic acid, which means it is not a salt).

As noted above, the reaction of equation (2) has been carried out by exposing solid alkali metal aryloxide to $CO_2$, typically in the temperature range of about 150–250° C. Usually some form of agitation or grinding is provided to expose all of the solid to the $CO_2$. The desired dialkali metal salt of the aromatic hydroxycarboxylic acid is a solid under these conditions, but the aromatic hydroxy compound formed is a liquid which often eventually boils or vaporizes off in the $CO_2$ (or other gas) stream. Thus the reaction often goes from a solid powder to a paste to a solid powder, and that combined with the difficulty of completely reacting a solid with a gas requires the reaction to be run for long periods of time to complete it.

It has been found that much shorter reaction times can be obtained if molten alkali metal aryloxide is reacted (contacted) with the $CO_2$, particularly with agitation. In this scenario, the initial material is a liquid which usually turns to a paste as the solid dialkali metal salt of the aromatic hydroxycarboxylic acid and the liquid aromatic hydroxy compound are formed. This usually gradually turns to a dry solid as the aromatic hydroxy compound is boiled or volatilized from the mixture.

Since it is desired to react the alkali metal aryloxide while it is in the molten state, the contacting with should be carried out about at or above the melting point of the alkali metal aryloxide. Since it will usually be desirable to eventually cool the resultant dialkali metal salt of the aromatic hydroxycarboxylic acid, up to the last 20 mole percent of the reaction with $CO_2$ may be carried out below the melting point of the alkali metal aryloxide, although it is preferred that at least 90 mole percent, more preferably at least 98 mole percent of this reaction be carried out about at or above the melting point of the alkali metal aryloxide.

In the contacting with $CO_2$, it is of course preferred that the alkali metal aryloxide or any of the other materials present during the process not decompose appreciably, i.e., be reasonably stable at the process temperature. Therefore it is preferred that the alkali metal aryloxide have a melting point of less than 400° C., more preferably less than about 350° C., and especially preferably less than about 320° C. A preferred minimum temperature is either the melting point of the alkali metal aryloxide or 275° C., whichever is higher.

In the reaction with $CO_2$, useful aryl groups include phenyl, 1-naphthyl, 2-naphthyl, 2-phenylphenyl, and 3-methylphenyl. Preferred aryl groups are phenyl, 2-phenylphneyl and 2-naphthyl, phenyl and 2-naphthyl are more preferred, and phenyl is especially preferred. Preferred alkali metal aryloxides are potassium phenoxide, sodium phenoxide, potassium 2-phenylphenoxide, potassium 2-naphthoxide, potassium phenoxide and potassium 2-naphthoxide are more preferred and potassium phenoxide is especially preferred. Preferred products (expressed as their parent aromatic hydroxycarboxylic acids, they are originally produced as their dialkali metal salts) are salicylic acid, p-hydroxybenzoic acid, 3-phenyl-4-hydroxybenzoic acid, and 6-hydroxy-2-napthoic acid, and p-hydroxybenzoic acid is especially preferred.

Suitable materials of construction for the $CO_2$ reaction are the same as described above for the drying of alkali metal aryloxides. Useful types of equipment for this reaction include, but are not limited to, a ribbon blender, the LIST-CRP and LIST ORP, made by LIST AG, Arisdorf, Switzerland, and available in various sizes, a Littleford VT Series vacuum dryer made by Littleford Day, Inc., Florence, Ky., U.S.A., or a Reactotherm RT made by Krauss-Maffei Verfahrenstechnik Gmbh, Munchen, Germany. The reaction may be run in a batch, semicontinuous or continuous manner. For instance a modified screw conveyor reactor may be used. Screw conveyor reactors are known in the art, see for instance B. Elvers, et al., Ed., Ullmann's Encyclopedia of Industrial Chemistry, Vol. B4, 5th Ed., VCH Verlagagesellschaft, Weinhem, 1992, p. 111–112. These are usually used in reactions where solids and liquids are involved. By a modified screw conveyor reactor is meant such a reactor wherein there is sufficient free volume that a gas may pass relatively freely through the reactor and be contacted with the solid and/or liquid ingredients present or its equivalent. Such a reactor may have single or multiple rotating shaft(s), or other agitating aids, such as high speed choppers. By an equivalent is meant any reaction apparatus that can move the liquid and/or solid reactants through the reactor at an appropriate rate (to give the desired residence time) while at the same time exposing fresh surfaces of the solid and/or liquid to the gaseous atmosphere, in this case containing $CO_2$. It should also have provision for adding one or more gases at one or more points along or through the reaction vessel, and preferably also have a port for removing any excess gas that is added to the system, and/or any volatiles generated during the process. Where a "screw-type" conveyor reactor is used, the "screws" of the reactor need not be solid screws, but may be segmented screws with open spaces between the screw shaft and the periphery of the screw. The screw or agitator shafts may be cored so that heat transfer fluid or $CO_2$ and/or other gas may be passed through. In the case of the $CO_2$ and/or other gas, there may be holes in the shaft(s) so that gas can pass through into contact with the reacting mass.

As mentioned above, the reaction of $CO_2$ with two equivalents of the alkali metal aryloxide yields one equivalent of the dialkali metal salt of the aromatic hydroxycarboxylic acid and one equivalent of the original aromatic hydroxy compound. In practice, the aromatic hydroxy compound is usually above its melting point at the process temperature and forms a paste with the dialkali metal salt formed and the solid (below its melting point) alkali metal aryloxide. This paste formation results in difficulty in mixing the $CO_2$ with the starting alkali metal aryloxide, thereby slowing the reaction. In addition, it is believed that the reactivity of the alkali metal aryloxide with $CO_2$ is reduced in the presence of the free aromatic hydroxy compound.

The formation of this paste is believed responsible for the long overall process cycles, usually at least several hours, experienced in the typical commercial Kolbe-Schmitt process, such as in a ball mill. In order to overcome this problem, a reactor which has an agitator that agitates the contents is desirable. The agitator and agitator drive (i.e., the power for the agitator) must be such that the agitator is sufficiently powerful to mix the contents of the reactors, especially in the paste phase of the reaction, so that relatively rapid reaction rates with $CO_2$ are maintained. Reactors such as are described above (when reacting molten alkali metal aryloxides) are suitable, and modified screw conveyor reactors (see above) are a preferred type of reactor. One such line of suitable modified screw conveyor reactors is the LIST-CRP and LIST ORP, made by LIST AG, Arisdorf, Switzerland, and available in various sizes. Another type of suitable reactor is a Reactotherm RT made by Krauss-Maffei Verfahrenstechnik Gmbh, Munchen, Germany.

The reactor should also have provision for adding one or more gases at one or more points along or through the screw conveyor system, and especially preferably also have a port for removing any excess gas that is added to the system, and/or any volatiles generated during the process.

It is preferred that the agitator of the reactor be essentially self cleaning, i.e., that essentially all material that may stick to the screw or barrel surfaces is wiped or otherwise removed from the surfaces so that it does not remain in the reactor for an excessive period of time. As mentioned above, the drive for the reactor should be powerful enough to overcome any drag that may be caused by the solids or any pastes that may form inside the reactor, so as to constantly mix the solid and/or liquids with the gas phase in the reactor, and not restrict the rate of reaction of $CO_2$.

Most Kolbe-Schmitt reactions are run at elevated temperatures, so there should usually be a means of heating the reactor. Such means are known to those skilled in the art, and include steam or other condensing vapors, hot liquid, electrical heat, etc.

The reaction may be run in a batch, semi-batch or continuous manner, and preferably the process is run in a continuous manner. Also preferably, the solid alkali metal aryloxide is fed at a first end of the reactor and continuously moves through the reactor to the second end of the reactor, where it exits the reactor. Preferably at least some of the $CO_2$ is added at the second end of the reactor and moves towards the first end of the reactor (preferably counter-currently to the movement of the solids and liquids in the reactor). More $CO_2$ may be added at other points along the reactor. Preferably the amount of $CO_2$ added is about stoichiometric (the amount required to react with the metal aryloxide added) to about 5 times the stoichiometric amount, more preferably about 2 to 4 times the stoichiometric amount.

Optionally, an inert gas such as nitrogen may also be added to the reactor. Excess $CO_2$ and/or the inert gas can help remove byproduct aromatic hydroxy compound which is formed during the reaction, thereby helping to reduce paste formation in the reactor. As mentioned above, it is believed that presence of aromatic hydroxy compound reduces the reaction rate of alkali metal aryloxide with $CO_2$, and therefore removal of the aromatic hydroxy compound is believed to result in an overall shorter process time.

It is also noted that many Kolbe-Schmitt reactions are run at temperatures above the atmospheric boiling points of many of the aromatic hydroxy compounds which are used. Thus even without the addition of excess $CO_2$ and inert gas to the reactor, much of the aromatic hydroxy compound may be removed by simple vaporization in many cases, so long as there is a vent port on the reactor. The heat of the reaction may be utilized to help vaporize the free aromatic hydroxy compound, further reducing cycle time and improving thermal efficiency.

It is preferred that the average residence time of the alkali metal aryloxide (or its reaction product with $CO_2$) in the reactor is less than about 1.5 h, more preferably less than about 1 hr, especially preferably less than about 0.5 h, and highly preferably less than about 0.25 h. In less than 2 h, or any of the times mentioned above, it is preferred that at least 80 mole percent, more preferably at least 90 mole percent, and especially preferably at least 95 mole percent, and most preferably at least 98 mole percent of the original alkali metal aryloxide has reacted with $CO_2$. By residence in a batch reactor is simply meant the reaction time for the batch. Average residence time in semi-batch and continuous reactions have their usual meanings.

Preferably, the interior of the reactor is at the ambient atmospheric pressure, plus or minus 20.0 kPa (0.2 bar). Pressures at or above the ambient pressure minimize the leakage of atmospheric gases such as oxygen or moisture into the reactor. Making such commercial reactors gas tight can be expensive and difficult.

Preferably the alkali metal is sodium or potassium, more preferably potassium. The preferred aryloxide anions for the process in the agitated reactor are the same as those listed above for the process involving drying and/or reaction of molten alkali metal aryloxides.

EXAMPLE 1

This example was carried out in the apparatus shown schematically in FIG. 1. The process was run in the CRP-6 batch reactor 1 into which nitrogen or carbon dioxide could be passed through rotameters 2 and associated valving 19 and 20 from nitrogen cylinder 3 and $CO_2$ cylinder 4, respectively. The amount of carbon dioxide passed through the reactor 1 was measured by noting the weight loss of the $CO_2$ cylinder 4 on the scale 5. The reactor 1 was heated by a circulating hot oil system 6 (including heater 7). Volatiles were removed by passage through a dust filter 8 and into a condenser 9. The condensed liquid then flowed through valves 17 to a receiver 10 (having a nitrogen inlet port 16) which could be weighed on the scale 11 to determine the amount of condensables recovered. The condensor 9 provides for water/glycol recirculation in the manner shown. Vacuum is established via a trap and exhaust/vacuum pump as shown. Throughout the figure, various temperature gauges "T1" and pressure gauges "P1" assist in monitoring the process. The reactor 1 is mounted on stand 18. Other useful associated valving 21 is shown in the Figure.

Pelleted potassium hydroxide (KOH, 4.16 kg) ("Baker analyzed, ACS Grade" material purchased from J. T. Baker company—minimum assay 85 wt % KOH with remainder mostly water) was loaded into a List, Inc. CRP-6 twin shaft mixing machine (CRP-6 batch reactor 1) provided with a hot oil system 6, vapor discharge port 12, and two gas injection ports 13, 14 as illustrated in the attached diagram. The entire system was evacuated to under 1.3 kPa pressure and refilled to atmospheric pressure with nitrogen gas a total of three times to remove oxygen from the KOH and the system atmosphere. Next, 5.97 kg of loose crystal phenol (PhOH, purchased from Lancaster Chemical Co.) were charged to the mixer through the charging port at the top of the vapor discharge port 12. The mixers were turned on for approximately 5 min to insure the phenol crystals dropped into the reactor 1, and the system evacuated to about 2.7 kPa pressure and refilled to atmospheric pressure with nitrogen a total of 3 times to remove any oxygen introduced with the phenol. At this time cooling water was supplied to the condenser 9, and the hot oil heater 7 set point was increased from room temperature to 225° C., and the mixer agitator drive set so that mixer speeds were 75 and 94 RPM on the slow and fast shafts, respectively of the CRP-6 batch reactor 1. Approximately 0.28 $m^3$/h of nitrogen sweep gas (metered by a rotameter 2 calibrated for air at STP) was provided during the heating portion of the experiment. The majority of this sweep nitrogen was injected on the side of the reactor 1 nearest the drive gearing. When the internal thermocouple in the unit indicated a temperature of approximately 120° C. the contents melted into a clear liquid (visible through a sight glass 15 on the end of the CRP-6 batch reactor 1 furthest from the gear drive) which we believe to be a solution of potassium phenoxide (PhOK) in water (both that brought in with the KOH and that liberated from the reaction of phenol and potassium hydroxide to form the phenoxide and water). When the contents temperature reached approximately 160° C. the solution began to boil and water began to collect in the receiver 10. When the solution temperature reached approximately 180° C. very vigorous boiling was observed throughout the volume of the solution. As the process temperature increased the solution appeared to rapidly increase in viscosity, and at a temperature of about 190° C. the solution appeared to begin solidifing. Once the solidification was complete water liberation slowed down markedly, and the hot oil heater 7 set point was increased to 325° C. Heating continued with slow evolution of water. When the process temperature approached 280° C. the solids began to melt giving a clear melt of potassium phenoxide with a small amount of dissolved water. When the process temperature was 290° C., the heating oil temperature controller (not shown) was set to 310° C., and the nitrogen sweep flow increased to 0.56 $m^3$/h. This elevated nitrogen flow was continued for 15 min during which an additional 0.064 kg of water was collected (total of 2.57 kg water collected).

At this point the CRP-6 batch reactor 1 was approximately 60% full of molten/dehydrated phenoxide. The nitrogen sweep gas flow was terminated and carbon dioxide flow at an indicated flow rate of 1.68 m³/h (measured by a rotameter calibrated for air at STP) was introduced thereinto. The carbon dioxide flow was divided into two streams. One was introduced into the vapor space above the phenoxide at the end of the reactor 1 furthest from the drive end, while the second stream was introduced slightly below the surface of the phenoxide at the end of the reactor 1 nearest the drive gearing. Approximately ⅔ of the carbon dioxide was introduced through the port nearest the gear drive, while about ⅓ was introduced through the other port. Shortly after introduction of the carbon dioxide gas a clouding of the previously clear melt was observed through the sight glass 15. Carbon dioxide gas was supplied at this rate over a period of 80 min during which time a total of 4.3 kg (weight measured with a digital scale) was charged to the CRP-6 batch reactor 1. During carbon dioxide charging the process temperature stayed relatively constant at 290° C. (±2° C.). For approximately the first 40 min of carbon dioxide charging relatively slow collection of phenol in the receiver 10 (total of 0.97 kg phenol collected over this time period) occurred, and the phenoxide melt became cloudier and cloudier, but continued to look like a low solids slurry. After about 40 min of carbon dioxide flow the material in the CRP-6 batch reactor 1 began to take on the appearance of a wet paste, and phenol collection rates began to rise, as did the hydraulic pressure needed to maintain fixed speed on the mixer agitators. Over the next 10 min an additional 0.74 kg of phenol were collected (giving a total of 1.71 kg), as the agitator hydraulic pressure returned to the same value seen during the earlier portions of the carbon dioxide flow. Shortly after that the paste seen through the sight glass 15 of the CRP-6 batch reactor 1 appeared to dry out, and a short burst of very high phenol evolution was observed. After 70 min of carbon dioxide flow a total of 2.79 kg of phenol had been collected, the product dipotassium p-hydroxybenzoate appeared as a dry/loose powder, and phenol evolution had markedly slowed. Over the next 10 minutes essentially no additional phenol was collected, and the process was terminated. Carbon dioxide gas injection was replaced with 0.28 m³/h of nitrogen gas (measured by a rotameter 2 calibrated for air at STP), and the controller for the hot oil heater 7 set to 10° C., and cooling provided for the circulating oil. Over the next 90 min the temperature of the process dropped to 45° C. At that time the mixer agitator was stopped, the nitrogen sweep gas flow shut down, and the circulating oil flow stopped. The reactor end plate was removed, and the powdered product removed for further testing. A total of 6.67 kg of solids were removed from the mixer 1. The majority of this (approximately 6.40 kg) was in the form of a free flowing cream colored powder, while some 0.27 kg was recovered as a lump in the vapor discharge line.

The powder was analyzed by High Pressure Liquid Chromatography using appropriate compounds for calibration. Before analysis the potassium salts were converted to the free compound. The analysis (based on the original weight of the sample) indicated there was 61.14 wt % PHBA (equivalent to 94.87 wt % of the dipotassium salt in the original sample) and 0.39 wt % phenol (equivalent to 0.56 wt % of potassium phenoxide in the original sample). No 4-hydroxyisophthalic acid or salicylic acid was detected.

EXAMPLE 2

Into a 1 liter 316 stainless steel resin kettle (purchased from Lab Glass Supplies) fitted with a 3 hole glass top were charged 131.8 g of potassium hydroxide (KOH) pellets (assay >85%). Once the pellets were charged, the charging funnel was replaced with a condenser tube and condensate receiver so any condensable vapors produced in the resin kettle would be condensed and collected in the receiver to keep them out of the resin kettle. The KOH pellets were evacuated to under 700 Pa pressure, and refilled with nitrogen to remove oxygen from the KOH. The resin kettle was suspended above a molten liquid metal bath during this period, and sufficient heat diffused into the steel vessel that the KOH pellets were observed to begin melting. Then 500 g of molten phenol was charged into a dropping funnel arranged so it could discharge directly into the process vessel through one of the holes in the top. A portion of the molten phenol was charged into the process. Initially a very vigorous reaction was noted, and the remaining phenol was charged very slowly with vigorous mechanical agitation of the vessel contents provided. The entire charge of KOH was fully melted/dissolved by completion of the phenol charging. After phenol charging was completed the dropping funnel was removed, and replaced with a bleed tube connected to house nitrogen. The molten metal bath was raised so about 40% of the height of the resin kettle was covered in liquid metal. Although the metal bath temperature controller was set at 170° C., the heat of reaction between the phenol and KOH raised the metal bath temperature to 205° C. The molten metal bath temperature controller set point was raised to 220° C. As heating proceeded, a milky condensate was collected. As the process temperature approached the metal bath temperature the condensate turned from milky to clear. Molten metal bath temperature controller set point was raised to 240° C., and the bath itself raised so over 80% of the height of the resin kettle was covered by liquid metal. The liquid metal bath temperature controller set point was raised to 300° C. over next 30 min, and the bath held at this temperature for about 1 h with a slow sweep of nitrogen to help remove water. After that time, the metal bath was lowered out of contact with the resin kettle, and its heater shut off. The temperature of the liquid in the resin kettle was measured to be 266° C. with a thermocouple. After the thermocouple was removed, the resin kettle was swept with a small flow of nitrogen as it cooled to room temperature. Liquid (304 g) was collected in the condensate receiver. The recovered solid was found to contain 1.1% water as measured by Karl Fisher titration.

EXAMPLE 3

Sodium hydroxide pellets (40 g) were charged to the same 1 liter stainless steel resin kettle described in Example 2, and evacuated to below 400 Pa and refilled with nitrogen to atmospheric pressure 3× to remove oxygen. Then, 100.0 g of loose crystal phenol charged to the nitrogen blanketed vessel through a powder funnel. The vessel was then evacuated to 6.6 kPa, and refilled to atmospheric pressure 2 times to remove oxygen. A nitrogen gas bleed was established across the vessel, condenser and condensate receiver to aid in removal of volatiles from over the reaction mass. A molten liquid metal bath held at 200° C. was then raised to cover 80% of the vertical height of the stainless steel resin kettle. The bath temperature controller was set to 318° C. and a mechanical agitator turned on. As the bath, resin kettle, and reaction mass was heated water and excess phenol were boiled out. The metal bath temperature reached 318° C. after approximately 35 min. Heating was continued for another 20 min, and then the molten metal bath was lowered, its heater shut off.

After the vessel had cooled to near room temperature it was opened and the contents examined. Visual examination indicated that the majority of the vessel contents had been molten at the time the experiment ended, although clearly a small fraction was in the form of a frozen powder. Differential scanning calorimetry on the material that had been in the molten phase indicated a sharp melting point at 272° C. Essentially no change occurred in the DSC trace after the sodium phenoxide had been heated to 180° C. and held for several hours in an evacuated oven.

EXAMPLE 4

Potassium hydroxide pellets (66.0 g) was charged to the same 1 liter stainless steel resin kettle described Example 2, and evacuated to below 400 Pa and refilled with nitrogen to atmospheric pressure 3× to remove oxygen. Then, 144.2 g of loose crystal 2-naphthol charged to the nitrogen blanketed vessel through a powder funnel. The vessel was then evacuated to 6.7 kPa, and refilled to atmospheric pressure 2 times to remove oxygen. A nitrogen gas bleed was established across the vessel, condenser and condensate receiver to aid in removal of volatiles from over the reaction mass. A molten liquid metal bath held at 200° C. was then raised to cover 80% of the vertical height of the stainless steel resin kettle. The bath temperature controller was set to 318° C. and a mechanical agitator turned on. As the bath, resin kettle, and reaction mass was heated water and excess phenol were boiled out. The metal bath temperature reached 318° C. after approximately 30 min. Heating was continued for another 30 min, and then the molten metal bath was lowered, and its heater shut off.

After the vessel was cooled to near room temperature it was opened and the contents examined. Visual examination indicated that essentially all of the vessel contents had been molten at the end of the heating period. Differential scanning calorimetry on the recovered potassium 2-naphthoxide indicated a sharp melting point at 243° C.

EXAMPLE 5

In this Example, an apparatus similar to that shown in FIG. 1 was used except there were no scales 5 and 11 to weigh the $CO_2$ added or the phenol recovered.

Potassium hydroxide (2.7 kg) and phenol (4.0 kg) were added to the CRP-6 batch reactor 1 under nitrogen, the reactor 1 was put under vacuum, and then under an ambient pressure of nitrogen and a nitrogen purge. Heating of the reactor was started and the two agitator shafts were set rotating and 30/37 rpm, and then 53/67 rpm. Water distilled during this period. When the contents temperature reached 255° C. a vacuum was applied for 25 min to remove the last traces of water. At this point there was a powder in the reactor 1.

Then at a reactor contents temperature of 255° C. $CO_2$ was added at the rate of 1.99–2.26 m³/h (70–80 SCF/h) for a period of 72 min (except for 2 short time periods when phenol plugs formed in the condenser 10). In addition, for the first 37 min of the $CO_2$ addition 0.57 m³/h (20 SCF/h) of nitrogen was also added. Except for the two brief periods when plugs were present in the condenser 10, the pressure in the reactor 1 was approximately ambient pressure. Shortly after the $CO_2$ addition started the reaction mass became pasty, and then gradually became a dry powder again as $CO_2$ addition progressed. Power consumption by the agitator drive also peaked shortly after $CO_2$ addition started and about the same time as the reaction mass got pasty. Power consumption thereafter decreased slowly. Product analysis is given in Table 1.

EXAMPLE 6

This Example was run exactly the same as Example 5 except drying and reaction with $CO_2$ was done at 272–274° C., $CO_2$ flow rate was 2.26 m³/h (80 SCF/h) for 58 min (there were no plugs of the system), and no nitrogen flow during $CO_2$ addition. Observations during the $CO_2$ addition were similar to those in Example 5. Product analysis is given in Table 1.

EXAMPLE 7

This Example was run exactly the same as Example 5 except drying and reaction with $CO_2$ was done at a reactor contents temperature of 269–271° C., drying was done under a flow of 0.57 m³/h (20 SCF/h) of nitrogen, and $CO_2$ addition was at 2.26 m³/h (80 SCF/h) for 67 min. Observations during the $CO_2$ addition were similar to those in Example 5. Product analysis is given is Table 1.

TABLE 1

In this Table yields are given as a percentage of the original total sample, in which the compounds were present as their alkali metal salts. The actual analysis was done by high pressure liquid chromatography (HPLC) on the free compounds, i.e., after they had been acidified, using appropriate standards. "Total Salts" is based on a back calculation using the HPLC analysis results of the total amount of the sample accounted for by the analysis. It is suspected the "missing" material is potassium (bi)carbonate and perhaps other inorganic salts. In the Table "N/D" means not detected.

TABLE 1

| | Example No. | | |
|---|---|---|---|
| | 5 | 6 | 7 |
| % PHBA | 59.82 | 52.86 | 58.36 |
| % Phenol | N/D | 0.57 | 1.43 |
| 4-hydroxyisophthalic acid (ppm) | 300 | 200 | 200 |
| Salicylic acid | N/D | N/D | N/D |
| Total Salts | 92.88 | 82.82 | 92.59 |

What is claimed is:

1. A process for drying an alkali metal aryloxide, comprising, finally removing water from said alkali metal aryloxide while said alkali metal aryloxide is molten.

2. The process of claim 1 wherein said alkali metal aryloxide is potassium phenoxide, sodium phenoxide, potassium 2-phenylphenoxide or potassium 2-naphthoxide.

3. The process of claim 1 wherein said alkali metal aryloxide is potassium phenoxide.

4. The process of claim 1 wherein said alkali metal aryloxide has a melting point of less than about 320° C.

5. The process of claim 1 carried out at a temperature of at least about 275° C.

6. The process of claim 1 wherein said alkali metal aryloxide becomes solid and then melts during drying.

7. The process of claim 1 wherein said alkali metal aryloxide remains molten while drying.

8. An improved process for the production of an aromatic hydroxycarboxylic acid using a Kolbe-Schmitt reaction of a metal salt of an aromatic hydroxy compound with carbon dioxide wherein a paste is produced during the reaction, wherein the improvement comprises, carrying out the reaction with carbon dioxide at a pressure of about 0.8 to 2 atmospheres, absolute, in a reactor whose contents are agitated and wherein there is sufficient free volume that a gas may pass relatively freely through the reactor and be contacted with solid and/or liquid ingredients present provided that:

the agitation is sufficient that the average residence time of a nongaseous reactant in said reactor is less than about 2 hours;

at least 80 mole percent of said metal salt of an aromatic hydroxy compound is reacted with said carbon dioxide in said reactor; and said gas which is unreacted exits said reactor.

9. The process of claim 8 wherein said metal is an alkali metal.

10. The process of claim 9 wherein excess carbon dioxide or an inert gas or both are added to said reactor.

11. The process of claim 9 which is run continuously.

12. The process of claim 9 which is run as a batch reaction.

13. The process of claim 9 wherein said carbon dioxide is added countercurrently to a movement of said solid in said reactor.

14. The process of claim 9 wherein at least 95 mole percent of said metal salt of an aromatic hydroxy acid is reacted with said carbon dioxide in said reactor.

15. The process of claim 9 wherein said total pressure is ambient atmospheric pressure, plus or minus 0.2 bar.

16. The process of claim 9 wherein said alkali metal is sodium or potassium.

17. The process of claim 9 wherein said alkali metal is potassium.

18. The process of claim 9 wherein said metal aryloxide is potassium phenoxide, sodium phenoxide, potassium 2-phenylphenoxide or potassium 2-naphthoxide.

19. The process of claim 9 wherein said metal aryloxide is potassium phenoxide.

20. The process of claim 9 wherein said metal aryloxide is potassium phenoxide or potassium 2-napthoxide.

21. The process of claim 9 carried out at a temperature at or above a melting point of said metal aryloxide or 275° C., whichever is higher.

22. The process of claim 9 wherein an aromatic hydroxy compound is removed during said process.

23. The process of claim 9 wherein said average residence time is less than about 1.0 h.

* * * * *